US00PP31379P3

(12) United States Plant Patent
Maillard et al.

(10) Patent No.: US PP31,379 P3
(45) Date of Patent: Jan. 21, 2020

(54) APRICOT TREE NAMED 'APRILOVE'

(50) Latin Name: ***Prunus armeniaca* L.**
Varietal Denomination: APRILOVE

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 16/350,461

(22) Filed: Nov. 20, 2018

(65) Prior Publication Data

US 2019/0159381 P1 May 23, 2019

(30) Foreign Application Priority Data

Nov. 23, 2017 (QZ) ..... PBR 2017/3040

(51) Int. Cl.
*A01H 5/08* (2018.01)
*A01H 6/74* (2018.01)

(52) U.S. Cl.
USPC ..... Plt./186
CPC ..... *A01H 6/7436* (2018.05)

(58) Field of Classification Search
USPC ..... Plt./180, 186
See application file for complete search history.

*Primary Examiner* — Susan McCormick Ewoldt
(74) *Attorney, Agent, or Firm* — Birch, Stewart, Kolasch & Birch, LLP

(57) ABSTRACT

A new and distinct variety of apricot tree, denominated 'APRILOVE', characterized by its self-fertility and no susceptibility to pests and diseases and by fruits of very good firmness, of very long shelf life without alteration after harvesting, and with an orange flesh, of high eating quality, aromatic, with a very high level of sugar, and with an attractive luminous orange red skin on a dark orange background.

3 Drawing Sheets

Botanical classification: *Prunus armeniaca* L.
Variety denomination: 'APRILOVE'.

This application claims priority of Community plant variety right No. 2017/3040 filed on Nov. 23, 2017, which is hereby incorporated by reference in its entirety.

BACKGROUND OF THE NEW VARIETY

The present invention relates to a new and distinct variety of apricot tree, *Prunus armeniaca* L., which has been given the variety denomination 'APRILOVE'. This new tree produces fruit with a long shelf life without alteration after harvesting, very good eating quality, and orange flesh fruit for fresh market in at the end of June or in July in the Pyrénées-Orientales department, France.

Contrast is made to 'APRIDELICE' (U.S. Plant Pat. No. 25,631), a similar apricot tree variety, for reliable description. Contrast is also made to the known female parent variety.

The new variety named 'APRILOVE' is a promising candidate for commercial success in that it has very attractive fruits with long shelf life without alteration after harvesting. This new variety results from our plant-breeding program aimed at obtaining self-pollinating apricot trees producing fruits of sweet and very aromatic taste, with an attractive orange skin covered by an appealing orange red blush. One of our main concerns is also the production of new varieties producing fruits having a long shelf life after harvesting, to facilitate long distance shipping. Our final purpose is the production of a range of new apricot tree varieties differing by their time of maturity, while producing fruits of very similar characteristics, to provide markets with almost indistinguishable fruits during the whole period of production of apricot.

ORIGIN OF THE VARIETY

The 'APRILOVE' apricot tree originated in a cultivated area of the south of France, in the Pyrénées-Orientales departement, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'APRILOVE' resulted from an open pollination of the apricot tree variety named 'ASFCOT0201' (U.S. Plant Pat. No. 24,093) which was used as the seed parent (female parent). Thus, the pollen parent remains unknown.

The 'APRILOVE' variety was propagated by grafting on a 'FRANC INRA® MONTCLAR' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of apricot tree blooms generally during the second half of March in the Pyrénées-Orientales departement, France. Sometimes, the blooming period begins earlier in March. More particularly, the blooming period generally starts from March $5^{th}$ to March $27^{th}$. However, it was observed that its early date of blooming seems to be highly dependant on climatic conditions.

The first fruit of 'APRILOVE' apricot tree ripens in June or early in July, generally later than the similar apricot variety named 'APRIDELICE' (U.S. Plant Pat. No. 25,631). However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
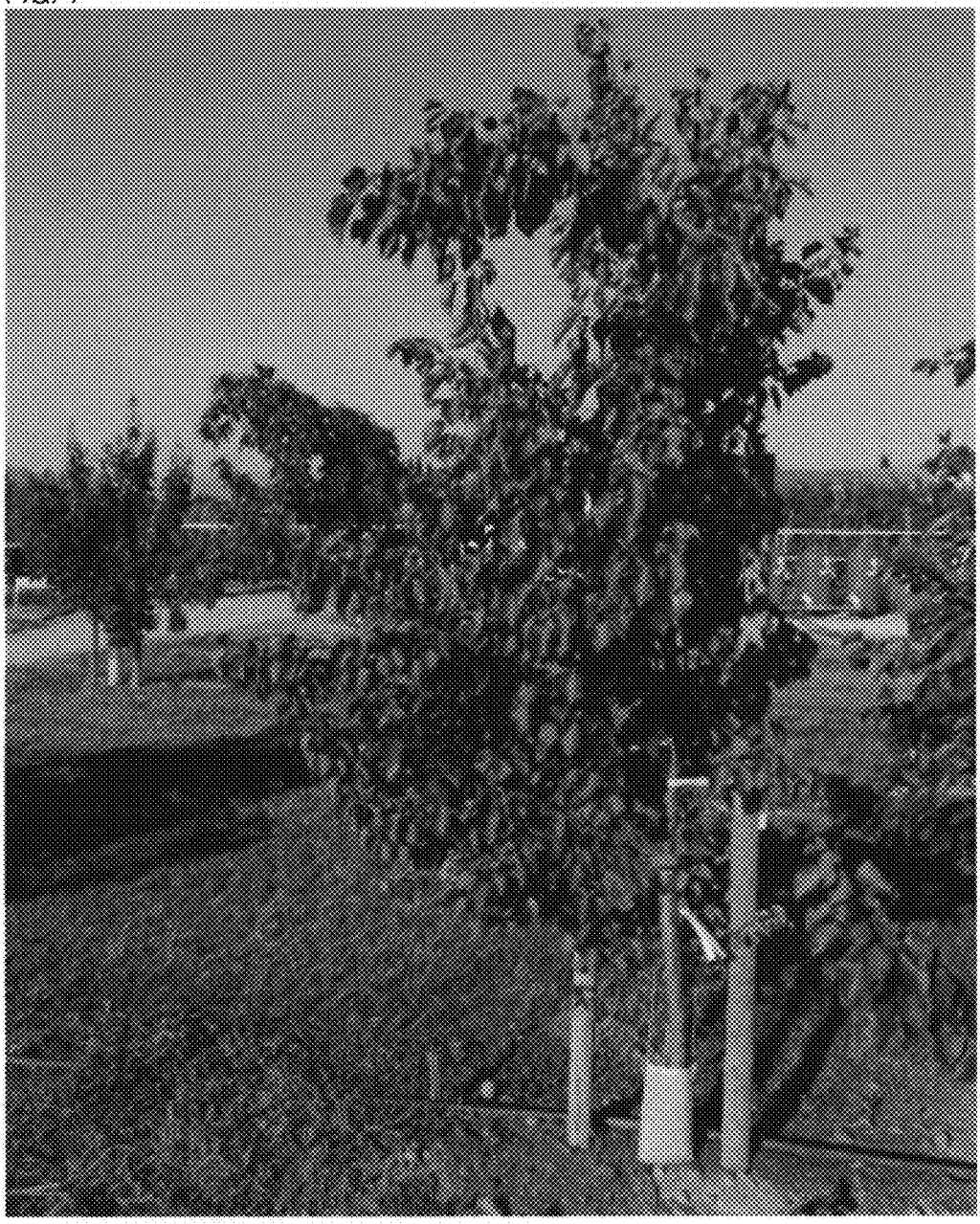
FIG. 1 is a color photograph, which shows a view of an apricot tree of the new variety 'APRILOVE' in orchard, bearing fruits.
Figure 2:
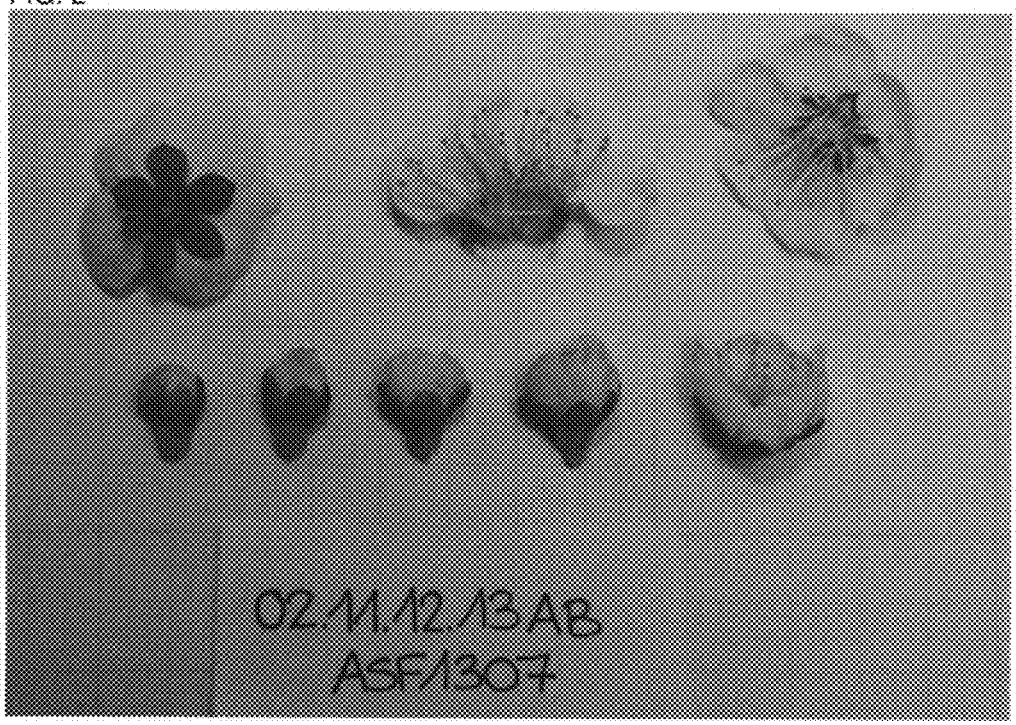
FIG. 2 is a color photograph, which depicts the flower buds at different development stages, and the reverse and side view of the flower and the reproductive organs with petals removed, of the new variety.
Figure 3:
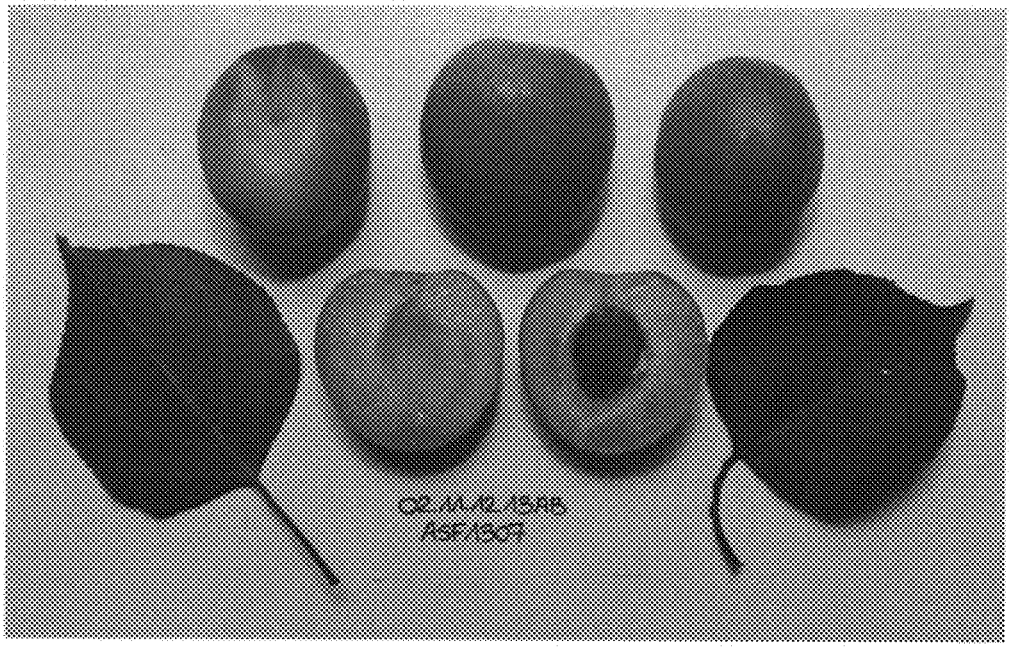
FIG. 3 is a color photograph, which shows the upper and lower sides of leaves and three whole fruits of the new variety 'APRILOVE', and a fourth fruit, cut in halves, with the stone left in one of the halves for depicting the fruit flesh the stone and the stone cavity of the new variety, as well as the leaves of the variety.
Figure 4:
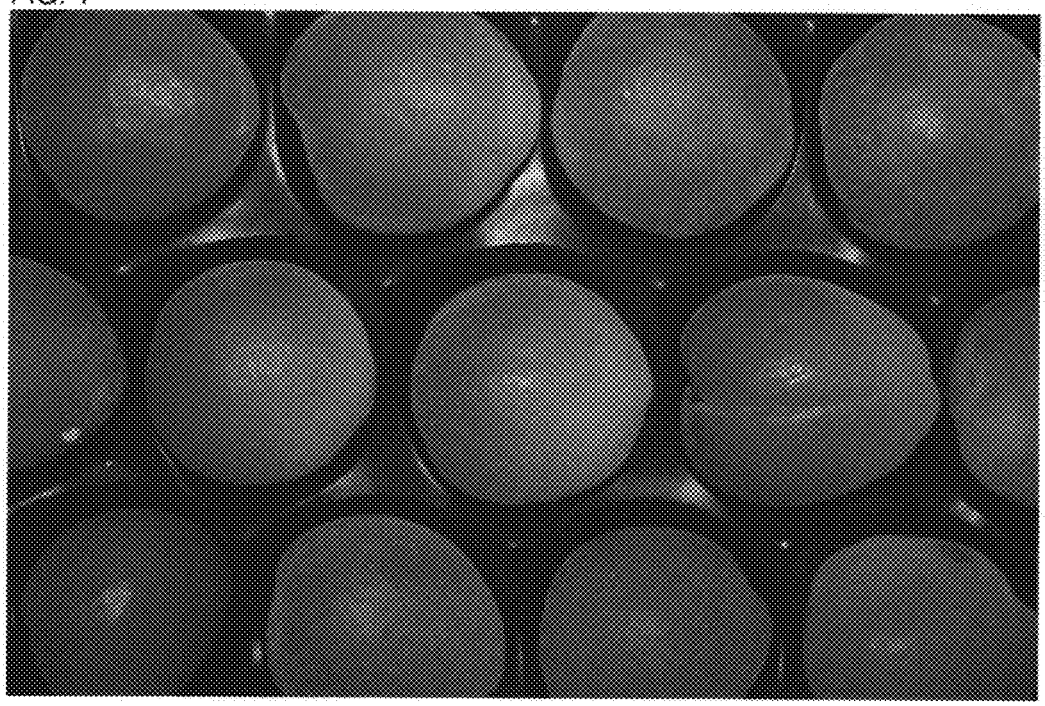
FIG. 4 is a color photograph showing a close view of typical specimens of the new variety 'APRILOVE' at ripening time.
Figure 5:
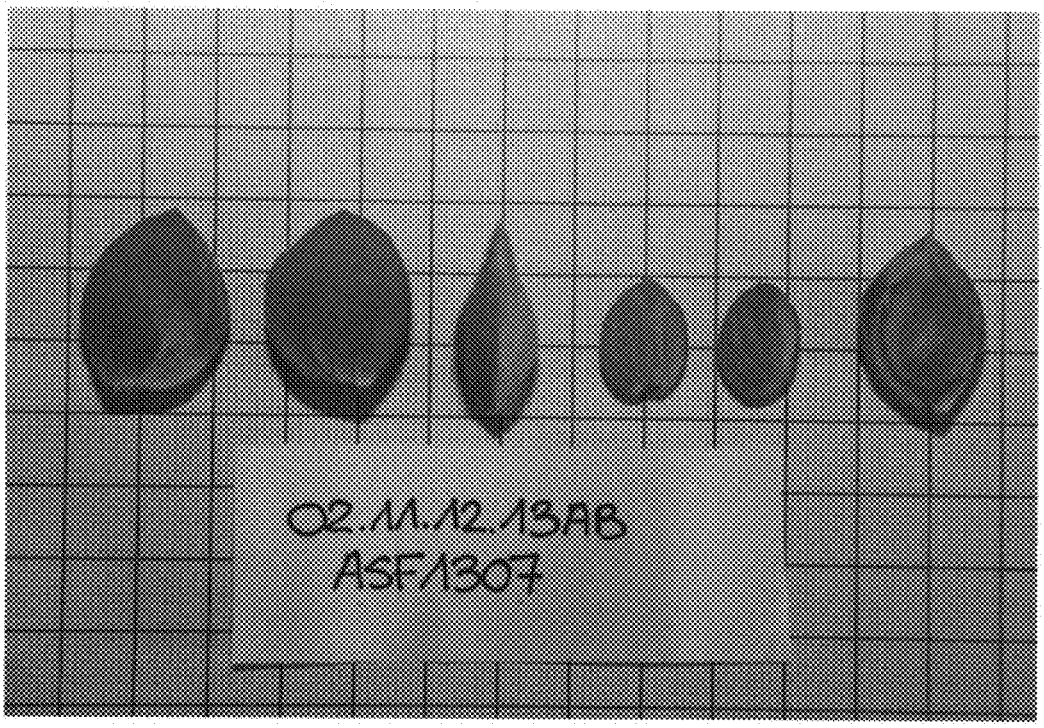
FIG. 5 is a color photograph showing different view of three whole stones of the new variety, and a third stone cut in halves for depicting the kernel of the stone and 2 kernels.

The enclosed photographs show plants in their third growing season for leaves, fruits, stones and plants in their fourth growing season for trees, trunk and flowers.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'APRILOVE' is high, due to fruit very long shelf life without alteration after harvesting.

Trees are medium vigorous and medium stature in a naturally semi-upright out aspect. The time of beginning of flowering is considered medium; flowering begins generally during the second half of the month of March. The flower petals are medium and colored in white or in an extremely pale pink. Leaf glands are present and round. Time of maturity for consumption is considered medium, namely at the end of June or early in July. The fruit flesh is considered orange. The fruit skin is medium thick and colored with an orange red blush on a orange background. The stone is medium size. Fruit taste is very aromatic and with a high level of sugar.

Compared to 'APRIDELICE' (U.S. Plant Pat. No. 25,631) apricot tree, the fruits of 'APRILOVE' variety ripens earlier, as set forth above. Moreover, the fruits of 'APRILOVE' are colored with an orange red blush covering 75 to 90% on the fruit skin surface, whereas the fruit produced by the similar variety 'APRIDELICE' show an orange red blush covering 65 to 75% of the skin surface. The fruits of the new variety 'APRILOVE' are considered very firm whereas the fruits of 'APRIDELICE' are firm. The flavour of the flesh is considered less sugary for 'APRIDELICE', compared to 'APRILOVE' flavour. More particularly, the fruit flesh of 'APRILOVE' has a very good taste, very sugary, between 20 and 27 brix. In comparison, the fruits of the 'APRIDELICE' variety have a good taste, sugary, with between 16 and 19 brix.

Compared to its seed parent 'ASFCOT0201' (U.S. Plant Pat. No. 24,093), 'APRILOVE' is a self-fertile variety. On the contrary, 'ASFCOT0201' (U.S. Plant Pat. No. 24,093) is considered sterile and needs to be pollinated by other varieties in order to get yearly production.

Moreover, compared to its seed parent 'ASFCOT0201' (U.S. Plant Pat. No. 24,093) the 'APRILOVE' variety ripens approximately two weeks earlier.

Moreover, the 'APRILOVE' variety produces very attractive fruits, with an orange red blush covering between 75 and 90% of the fruit skin, on an orange background. In comparison, 'ASFCOT0201' (U.S. Plant Pat. No. 24,093) apricot tree produces fruits with a blush covering 40 to 60% of the skin, on a yellow orange background.

DETAILED DESCRIPTION

Referring more specifically to the pomological details of this new and distinct variety of apricot tree, the following was observed on trees in their third growing season (second year of production) for leaves, fruits, stones and plants in their fourth growing season (third year of production) for trees, trunk and flowers under the ecological conditions prevailing at the orchards located near the town of Elne, Pyrénées-Orientales departement, France. All observations have been done on rootstock cultivars. Used rootstocks were 'FRANC INRA® MONTCLAR' (non patented) trees. All major color code designations are by reference to The R.H.S. Colour Chart (Fourth Edition) provided by The Royal Horticultural Society of Great Britain.

Tree:

*Size.*—.

*Generally.*—Considered medium as compared to other common commercial apricot cultivars. Trees reach about 250 cm during the first growing season. Trees were pruned during each following season to a height of approximately 250 cm and to a diameter of 200 cm.

*Spread.*—Approximately 200 cm. The whole orchard was oriented to a central leader organization, with tree lines spaced of 4.0 meters and trees spaced of 1.0 meter in a same tree line.

*Vigor.*—Considered medium vigorous. Current season shoots growth could reach 100 cm. During the first year of growth, trees growth reaches 250 cm. In the second and following seasons, the size of trees is reduced to 250 cm by pruning. However, these characteristics are dependant on soils fertility, cultural practices, and prevailing climatic conditions.

*Productivity.*—The productivity is considered good, and regular. Fruit set is spaced by thinning to develop the remaining fruit into the desired market sized fruit. Because of the fruit size, the new variety only requires a medium thinning for the tree valorisation. Thinning was necessary every year during the years of observation. The number of the fruit set varies with the prevailing climatic conditions and cultural practices employed during the bloom period and is therefore not distinctive of the present variety.

*Bearer.*—Very regular. No alternate bearing was observed.

*Form.*—The 'APRILOVE' variety has a naturally semi-spreading shape.

*Density.*—Considered highly dense, in order to obtain and observe fruits more quickly.

*Hardiness.*—The present tree was grown and evaluated in France. The variety appears to be hardy under the central Pyrénées-Orientales departement typical climatic conditions. Experimentations on the same orchard in Elne, Pyrénées-Orientales department, with winter chilling requirement below 7.2° C. comprised between 350 hours and 1200 hours according to the specificities of the year, namely 1031 hours in 2012-2013, 777 hours in 2013-2014, 893 hours in 2014-2015, 718 hours in 2015-2016, and 825 hours in 2016-2017 and 1017 hours in 2017-2018 showed a good behaviour of the tree in all cases. No damages were caused by ascertained temperatures as low as −12 degrees Celsius in winter. The tree was also very resistant to frosty springtime weather.

Trunk:

*Diameter.*—Approximately 75.0 to 80.0 millimeters in diameter when measured at a distance of approximately 20.0 centimeters above the soil level.

*Bark texture.*—Considered rough with lenticels.

*Bark coloration.*—The bark has mostly a light brown color (RHS Greyed Orange 177 A).

*Lenticels.*—.

*Lenticel color.*—A beige color (RHS Greyed Orange 164 C to RHS Greyed Orange 164 D).

*Density.*—The number of lenticels is approximately 3 lenticels per $cm^2$.

*Size.*—Lenticels are approximately 2.0 to 2.5 millimeters in width and 3.0 to 4.5 millimeters long.

Branches:

*Size.*—The branches are pruned every year to approximately 1.0 meter in length.

*Diameter.*—Average as compared to other apricot varieties. The current season shoots have a diameter of about 5.0 to 7.0 millimeters, and mature branches have a diameter of about 9.0 to 12.0 millimeters.

*Surface texture.*—Current season shoots have a smooth texture. Mature branches are medium rough. Roughness increases with trees age. Wood which is several years old has furrowed appearance.

*Crotch angles.*—The crotch angles are generally 30 degrees from the trunk axis, for current season shoots. At maturity, the crotch angle increases with fruits weight, until 50 degrees. This particular characteristic is not considered distinctive of the variety, however.

*Current season shoots.*—.

*Internode length.*—Generally 8.0 to 11.0 millimeters.

*Color of current season's shoots.*—Considered light brown to green (RHS Grey Brown N199 A) on lower part of new shoot tips, whereas the upper part is darker and colored in brown (RHS Greyed Orange 166 A). The current season's shoots color evolves and turns to mature branches color when aging.

*Mature branches.*—.

*Internode length.*—Generally 12.0 to 15.0 millimeters.

*Color of mature branches.*—Light brown (RHS Greyed Orange 165 A).

*Vigor.*—Considered spread as for all the apricot varieties.

*Lenticels.*—.

*Density.*—Lenticels are present, just as on the trunk, especially on mature branches. More particularly, 6 lenticels appear per $cm^2$ on mature branches.

*Size.*—Considered small, and slightly smaller than trunk's lenticels, they are approximately 1.5 to 2.0 millimeters wide and 0.5 to 1.0 millimeter height.

*Color.*—Considered beige color (RHS Greyed Orange 164 B or RHS Greyed Orange 164 C).

*Form.*—Round and stretched.

Leaves:

*Size.*—Considered medium for the species.

*Leaf length.*—The leave's length is between 75.0 and 90.0 millimeters with leaf petiole. The medium length is 81.8 millimeters.

*Leaf width.*—The leave's width is between 67.0 and 75.0 millimeters. The medium width is 71.0 millimeters.

*Leaf form in cross section.*—Concave.

*Leaf form.*—Almost circular.

*Leaf tip form.*—Acuminate.

*Leaf base form.*—Generally truncate.

*Leaf margins.*—Considered dentate.

*Thickness.*—Medium.

*Upper surface texture.*—Smooth.

*Lower surface texture.*—Smooth.

*Leaf color.*—.

*Upper leaf surface.*—The color of the upper leaf surface is green (RHS Yellow Green 147 A).

*Lower surface.*—A lighter green than the upper leaf surface color. The lower surface of leaves is RHS Yellow Green 147 B.

*Leaf venation.*—Pinnately veined.

*Mid-vein.*—.

*Thickness.*—Approximately 1.5 millimeters when measured at the base of the leaf.

*Color.*—Red purple (RHS Red Purple Group 59 B).

*Other veins color.*—Light green (RHS Green Group 143 B).

*Uniformity.*—Leaves are of medium size and generally found alone. No stipules are generally found.

*Leaf petioles.*—.

*Size.*—Generally long.

*Length.*—The leaf petiole length is between 36.0 and 42.0 millimeters.

*Diameter.*—Approximately 2.0 millimeters.

*Surface.*—Smooth.

*Petioles colour.*—.

*Upper petiole surface.*—Depending on climatic conditions and sunlight exposure, the anthocyanic coloration on petiole's upper surface is generally considered red (RHS Red Group 53 B) to purple red (RHS Red Purple Group 59 B).

*Lower petiole surface.*—Light green (RHS Yellow Green 145 A).

*Leaf glands.*—.

*Size.*—Considered small.

*Length.*—Approximately 1.5 millimeters.

*Width.*—Approximately 1.0 millimeter.

*Number.*—Between 2 and 4 glands per leaf, sometimes 5 glands per leaf.

*Type.*—Circular.

*Margins.*—Smooth and regular.

*Position.*—Alternate between upper portion of petiole and lower portion of leaf blade.

*Color.*—Generally grey orange (RHS Greyed Orange Group 165 A).

*Leaf stipules.*—.

*Generally.*—No leaf stipules were observed.

Flowers:

*Flower buds.*—.

*Generally.*—At pre-floral stage of development, the floral buds are conic in form with a very rounded tip (ball shaped). Their form is evolving until blooming, with variables dimensions. At the pre-floral stage, the size of flower buds is 9.0 to 11.0 millimeters wide and approximately 14.0 to 16.0 millimeters long. Just before blooming, floral buds are approximately 12.0 millimeters wide and approximately 17.0 millimeters long. Generally, a bud is found alone or in group of two or three buds. The distribution of the flower buds is considered homogenous on the trees.

*Color.*—This characteristic is dependent upon the proximity to bloom. At pre-floral stage of development, the bottom of the flowers buds, or calyx, or flower receptacle, is of purple (RHS Red 46 A) or purple-brown color (RHS Greyed Purple 184 B to RHS Greyed Purple 184 C) on its outer face. The inner surface of the calyx is considered orange (RHS Orange N25 A to RHS Orange N25 B). The corolla, formed by the petals, is generally of white (RHS White Group N 155 B or RHS White Group N 155 C) to pale pink color (RHS Greyed Purple 186 D or RHS Red Purple 62 D) on both surfaces of the petals. The petal color generally evolves until the end of the blooming period, becoming whiter and whiter.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—During March, sometimes early in April.

*First bloom.*—The first bloom was observed on Mar. 26, 2013.

*Petal fall.*—Apr. 6, 2013.

*Blooming time.*—Considered medium season in relative comparison to other commercial apricot cultivars grown in the Pyrénées-Orientales departement, France. Thus, the first blooming time was from March 26$^{th}$ until Apr. 6, 2013, then from March 12$^{th}$ until Mar. 20, 2014, then from March 27$^{th}$ until Apr. 2, 2015, then from March 19$^{th}$ until Mar. 29, 2016 and then from March 5$^{th}$ until Mar. 17, 2017.

*Duration of bloom.*—Medium, approximately between 7 and 13 days.

*Spurs.*—.

*Lenticels.*—A few lenticels are present, more particularly between 2 to 7 per linear centimeter, but their number may vary with environmental conditions.

*Form.*—Ovate.

*Length.*—Approximately 2.0 millimeters.

*Width.*—Approximately 1.5 millimeters.

*Color.*—Orange grey (RHS Greyed Orange 165 A).

*Flower type.*—The variety is considered to have a showy type of flower (rosette).

*Flower size.*—Medium. Flower diameter at full bloom is approximately 28.0 to 34.0 millimeters.

*Bloom quantity.*—Considered abundant to very abundant, between 40 and 45 flowers per linear meter. Flowers are generally found in bunches.

*Flower bud frequency.*—Generally 1 flower bud or several flower buds per groups of 2 to 3.

*Petal size.*—.

*Generally.*—Medium.

*Length.*—Generally between 12.0 and 16.0 millimeters.

*Width.*—Generally between 13.0 and 18.0 millimeters.

*Petal form.*—Round-shaped.

*Petal count.*—Generally 5, and sometimes more than 5, namely 6 petals. The petals are separated when 5 petals are present and overlapping or slightly overlapping when six petals are present.

*Petal texture.*—Smooth, soft and glabrous. Sometimes, petals are very slightly creased.

*Petal color.*—At the stage F of blooming, when the flower is fully opened, both surfaces of petals are colored with a white (RHS White Group N 155 B or RHS White Group N 155 C or RHS White Group N 155) to a very light pink (RHS Greyed Purple Group 186 D) color.

*Fragrance.*—Sweet.

*Petal claw.*—.

*Form.*—Narrow.

*Length.*—About 1.0 to 1.5 millimeters.

*Width.*—About 1.5 millimeters at the base.

*Color.*—Generally the claw is colored like petal color (RHS White Group N 155 B to RHS White Group N 155 C to RHS White Group N 155 D or RHS Greyed Purple Group 186 D), sometimes to a very light pink (RHS Greyed Purple Group 186 D) color and darker than the petal color (RHS Red Purple 60 C).

*Petal margins form.*—Smooth and sometimes slightly wavy especially near the base.
*Petal base.*—Narrow at point of attachment.
*Petal apex.*—Wide-dome shaped.
*Petal peduncle.*—.
*Length.*—Approximately 2.5 to 4.0 millimeters.
*Diameter.*—Approximately 1.0 to 3.0 millimeters.
*Color.*—Generally light green (RHS Yellow Green 145 B or RHS Yellow Green C) and covered with small overlapping scales colored purple brown (RHS Greyed Red 178 A or RHS Greyed Red 178 B) to orange brown (RHS Greyed Orange 175 A or RHS Greyed Orange 175 B).
*Sepals.*—.
*Generally.*—Star shaped around the corolla base.
*Size.*—Considered medium.
*Length.*—Approximately between 5.0 and 7.0 millimeters.
*Width.*—Approximately between 4.0 and 6.0 millimeters.
*Sepal count.*—Generally 5, sometimes 6 sepals.
*Form.*—Almost triangular, with a slightly pointed apex.
*Margins.*—Smooth.
*Color.*—At the stage F of blooming, when the flower is open, the lower surface of the sepals is considered of purple color (RHS Greyed Purple 185 A or RHS Greyed Purple 185 B or RHS Greyed Purple 185 C or RHS Greyed Red 184 B). The upper surface of the sepals is colored in purple (RHS Red 46 A).
*Surface texture.*—Smooth and glabrous.
*Stamens.*—.
*Average number of stamens per flower.*—Between 25 and 36.
*Size.*—Approximately between 9.0 and 14.0 millimeters in length, generally higher than pistil's length, when not equal.
*Color.*—White (RHS White N155 D or RHS White Group 155 B or RHS White Group 155 C).
*Anthers.*—.
*Size.*—Generally small to medium in length.
*Shape.*—Cordate.
*Color.*—Yellow (RHS Yellow 11 A) to orange yellow (RHS Yellow Orange 16 A to RHS Yellow Orange 16 B), which may evolve with maturity.
*Pistil.*—.
*Number.*—Usually 1.
*Length.*—Approximately 16.0 to 19.0 millimeters including the ovary. The pistil's length is generally smaller or equal than stamen's length, the pistil being considered without the ovary.
*Color.*—Considered very pale green (RHS Yellow Green 150 D or RHS Yellow Green 145 C to RHS Yellow Green 145 D) to white (RHS White Group 155 C) depending on the maturity stage.
*Pollen.*—.
*Pollen production.*—Pollen production is considered good. The variety is self-fertile.
*Color.*—Yellow (RHS Yellow 7 B) to orange yellow color (RHS Yellow Orange 16 A to RHS Yellow Orange 16 B).
*Calyx.*—.
*Internal surface texture.*—Smooth and glabrous.
*Color.*—At the stage F of blooming, the inner surface of the calyx, namely the flower receptacle, is considered yellow orange (RHS Yellow Orange 17 A or RHS Yellow Orange 23 A) whereas the outer surface is purple (RHS Greyed Purple 185 B or RHS Greyed Purple 185 C or RHS Red 46 A) becoming slightly lighter near calyx base and light green near the peduncle.
*Ovary.*—.
*Pubescence.*—Present.
*Height.*—Between 3.0 and 4.0 millimeters.
*Diameter.*—Between 1.5 and 2.0 millimeters.
*Color.*—Light green (RHS Yellow Green 145 C to RHS Yellow Green 145 D).
*Stigma.*—.
*Position compared to anthers.*—The stigma is below the anthers, or at the same level.
*Diameter.*—Approximately 1.0 millimeter.
*Color.*—Yellowish (RHS Greyed Yellow 162 A).

Fruit:

*Maturity.*—Considered medium. Generally, fruits become mature during June or early in July.
*Date of first picking.*—Jul. 5, 2013.
*Date of last picking.*—The date of harvest varies slightly with the prevailing climatic conditions. The 'APRILOVE' variety has a medium date of picking and a grouped maturity. The maturity is usually grouped within 6 to 9 days and the harvest is generally performed in two runs. The first picking was carry on from July 5$^{th}$ to Jul. 11, 2013, then from June 14$^{th}$ to Jun. 20, 2014. The next picking times were from June 17$^{th}$ to Jun. 22, 2015, and from July 4$^{th}$ to Jul. 9, 2016, then from June 20$^{th}$ to Jun. 28, 2017 and then from June 26$^{th}$ to Jul. 1, 2018.
*Size.*—.
*Generally.*—Considered medium to large (size 2A+).
*Length.*—Approximately and between 49.0 and 57.0 millimeters.
*Width.*—Approximately between 50.0 and 54.0 millimeters.
*Thickness.*—Approximately between 46.0 and 48.0 millimeters.
*Typical weight.*—Generally between 70.0 and 80.0 grams. This characteristic is high dependent especially upon the prevailing cultural practices, and therefore is not particularly distinctive of the variety.
*Fruit form.*—.
*Generally.*—Round and slightly oblong near the apex and at the fruit base. The fruit is considered to be symmetrical.
*Suture.*—.
*Generally.*—Very slightly marked, extending from the base to the apex.
*Color.*—The suture has generally a color similar to the whole fruit color. Thus, the suture is colored with an orange red color (RHS Orange red N34 A).
*Ventral surface.*—.
*Form.*—Round to slightly flattened.
*Apex.*—Flat to slightly retuse.
*Base.*—Straight to slightly retuse.
*Stem cavity.*—Shallow. Average depth of the stem cavity is about 8.0 to 10.0 millimeters. Average width is about 12.0 to 15.0 millimeters.
*Stem.*—.
*Size.*—Generally small and short. Stem length is about 5.0 millimeters. Stem diameter is about 3.0 millimeters.

*Color.*—Stem color is generally green (RHS Yellow Green 145 A or RHS Yellow Green 145 B).

*Fruit skin.*—.

*Thickness.*—Considered medium, adherent and resistant.

*Texture.*—Smooth.

*Pubescence.*—Present but very light, almost non-existent.

*Tendency to crack.*—None observed.

*Color.*—.

*Blush color.*—This blush color is orange red (RHS Orange Red N34 A). The orange red blush covers between 75 and 90% of the fruit skin surface for fruits that are exposed to sunlight. The percentage of the blush on the fruit skin surface can vary and is generally dependent upon the prevailing conditions under which the fruit was grown.

*Ground color.*—The ground color covers 10 to 25% of the fruit skin surface, and is considered orange (RHS Orange 25 B).

*Adherence to flesh.*—Very adherent.

*Taste.*—Moderately acid and sugary.

*Flesh.*—.

*Ripens.*—The maturing of the fruit is uniform.

*Texture.*—Fine and firm. Very melting and juicy at end of maturity.

*Fibers.*—Generally none observed.

*Aroma.*—Very present, pronounced.

*Firmness.*—Firm. Holds firmness over the time.

*Eating quality.*—Considered very good and with a high level of sugars.

*Flavor.*—Considered very good. Semi sweet and with a good balance between sugar and acidity. Very aromatic.

*Juice.*—Very juicy. The juiciness increases with maturity.

*Brix.*—Generally superior to 20.0 degrees, between 20.0 and 27.0 degrees. This characteristic varies slightly with the number of fruits per tree, prevailing cultural practices and the surrounding climatic conditions.

*Flesh color.*—Considered medium orange (RHS Orange 25 B).

Stone:

*Stone cavity.*—.

*Color.*—The stone cavity shows the same orange color (RHS Orange 25 B) as the flesh color.

*Length.*—Similar to the stone's length, approximately between 27.0 and 30.0 millimeters.

*Stone type.*—Free, but the stone seems to be slightly attached to the flesh through its base.

*Size.*—Considered medium for the variety. The stone size varies depending upon the tree vigor, crop load and prevailing growing conditions.

*Length.*—Approximately 27.0 millimeters.

*Width.*—Approximately 20.0 millimeters.

*Diameter.*—Approximately 12.0 millimeters.

*Stone form.*—Ovoid.

*Stone form* (*viewed from stem end*).—Ovate flattened.

*Stone form* (*lateral view*).—Oblong.

*Stone base shape.*—Round to slightly concave.

*Stone apex shape.*—Round, generally not pointed.

*Symmetry.*—Symmetric.

*Stone surface.*—.

*Surface texture.*—Smooth to slightly rough.

*Ridges at stone surface.*—The ridges are present on both sides of the stone. A ridge is generally narrow. The ridges begin at the base and are extending all along the stone length.

*Stone color.*—The color of the dry stone is generally considered a greyed orange (RHS Greyed Orange 164 B to RHS Greyed Orange 164 C).

*Tendency to split.*—Splitting is absent.

*Kernel.*—.

*Taste.*—Bitter.

*Size.*—Medium.

*Length.*—Approximately 17.0 millimeters.

*Width.*—Approximately 12.0 millimeters.

*Thickness.*—Approximately 6.0 millimeters.

*Form.*—Ovate.

*Color.*—The kernel skin is a greyed orange (RHS Greyed Orange 164 B or RHS Greyed Orange 164 C or RHS Greyed Orange 165 B). The almond, which is the seed of the kernel, is considered white (RHS White 155 D) and has a bitter taste.

*Use.*—The subject variety 'APRILOVE' is considered to be an apricot tree with a medium season maturity, and which produces fruits that are considered very firm (the firmer among all our varieties), attractively and luminously colored with a high proportion of orange red blush covering the skin surface. Fruits have a balanced taste between acidity and sugar. They are excellent for uncooked or cooked consumption, melting and juicy when at full maturity. Fruits have excellent gustative qualities and are very aromatic. They are also useful for both local markets and very long-distance shipping.

*Keeping quality.*—Good. Fruits are well preserved during at least 3 weeks after harvest in a cold atmosphere. Fruits are considered to have a long shelf life after harvesting without alteration. After 4 weeks stored at 3° C., the fruits were still quite firm, very juicy and with a very good eating quality.

*Shipping quality.*—Considered good. The fruits of the new apricot variety showed very little skin scarring or flesh bruises in picking, packing and shipping trials.

*Resistance to insects and disease.*—No particular susceptibilities were noted. Under meticulous observations during planting, growing and harvesting of fruits, no particular resistance or sensitivity to plant or fruits diseases were noticed. Any variety, observed during indexing of plant characteristics, with abnormal fungus, bacterial virus or insect sensitivity is destroyed and eliminated from our breeding program.

Although the new variety of apricot tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of apricot tree as illustrated and described, characterized by its self-fertility and no susceptibility to pests and diseases and by fruits of very good firmness, of very long shelf life without alteration after harvesting, and with an orange flesh, of high eating quality, aromatic and with a very high level of sugar, and with an attractive luminous orange red skin on a dark orange background.

* * * * *